United States Patent [19]

Brazzell et al.

[11] Patent Number: 5,563,171
[45] Date of Patent: Oct. 8, 1996

[54] TREATMENT OF GLAUCOMA AND OCULAR HYPERTENSION WITH β3-ADRENERGIC AGONISTS

[75] Inventors: Romulus K. Brazzell, New City, N.Y.; Bernard Dubnick, Westwood, N.J.

[73] Assignee: American Cyanamid Company, Wayne, N.J.

[21] Appl. No.: 148,153

[22] Filed: Nov. 5, 1993

[51] Int. Cl.⁶ .................................................. A61K 31/36
[52] U.S. Cl. ............................................................ 514/465
[58] Field of Search ............................................... 514/465

[56] References Cited

U.S. PATENT DOCUMENTS

| | | |
|---|---|---|
| 4,309,443 | 1/1982 | Smith et al. |
| 4,329,358 | 5/1982 | Ainsworth et al. |
| 4,338,333 | 7/1982 | Ainsworth et al. |
| 4,341,793 | 7/1982 | Ferris |
| 4,382,958 | 5/1983 | Duckworth |
| 4,385,066 | 5/1983 | Ainsworth et al. |
| 4,391,826 | 7/1983 | Mills et al. |
| 4,432,993 | 2/1984 | Ferris |
| 4,568,691 | 2/1986 | Marsham et al. |
| 4,585,796 | 4/1986 | Alig et al. |
| 4,588,749 | 5/1986 | Ferris |
| 4,593,023 | 6/1986 | Hindley |
| 4,596,800 | 6/1986 | Ainsworth et al. |
| 4,602,044 | 7/1986 | Schmiegel et al. |
| 4,622,342 | 11/1986 | Cantello et al. |
| 4,629,737 | 12/1986 | Cantello |
| 4,652,679 | 3/1987 | Alig et al. |
| 4,654,371 | 3/1987 | Ainsworth et al. |
| 4,683,312 | 7/1987 | Dominianni et al. |
| 4,692,465 | 9/1987 | Hindley et al. |
| 4,695,580 | 9/1987 | Ohashi et al. |
| 4,707,497 | 11/1987 | Cecchi et al. |
| 4,772,631 | 9/1988 | Holloway et al. |
| 4,783,460 | 11/1988 | Cantello |
| 4,803,293 | 2/1989 | Berge et al. |
| 4,871,755 | 10/1989 | Alig et al. |
| 4,892,886 | 1/1990 | Alig et al. |
| 4,927,836 | 5/1990 | Holloway et al. |
| 4,977,148 | 12/1990 | Holloway et al. |
| 4,992,473 | 2/1991 | Anderson et al. |
| 4,999,377 | 3/1991 | Caulkett et al. |
| 5,017,619 | 5/1991 | Alig et al. |
| 5,045,567 | 9/1991 | Kienzie |
| 5,061,727 | 10/1991 | Bloom et al. |
| 5,106,867 | 4/1992 | Bloom et al. ............ 514/465 |
| 5,153,210 | 10/1992 | Ainsworth et al. |
| 5,166,218 | 11/1992 | Alig et al. |
| 5,202,466 | 4/1993 | Boigegrain et al. |

FOREIGN PATENT DOCUMENTS

| | | |
|---|---|---|
| 0061907 | 10/1982 | European Pat. Off. |
| 0063004 | 10/1982 | European Pat. Off. |
| 0068669 | 1/1983 | European Pat. Off. |
| 0070133 | 1/1983 | European Pat. Off. |
| 0089154 | 9/1983 | European Pat. Off. |
| 0091749 | 10/1983 | European Pat. Off. |
| 0095827 | 12/1983 | European Pat. Off. |
| 0102213 | 3/1984 | European Pat. Off. |
| 0164700 | 12/1985 | European Pat. Off. |
| 0171702 | 2/1986 | European Pat. Off. |
| 0170121 | 2/1986 | European Pat. Off. |
| 0196849 | 10/1986 | European Pat. Off. |
| 0254856 | 2/1987 | European Pat. Off. |
| 0233686 | 8/1987 | European Pat. Off. |
| 0262785 | 4/1988 | European Pat. Off. |
| 0386603 | 9/1990 | European Pat. Off. |
| 0386920 | 9/1990 | European Pat. Off. |
| 0500443 | 8/1992 | European Pat. Off. |
| 0066351 | 12/1992 | European Pat. Off. |
| 0516349 | 12/1992 | European Pat. Off. |
| 0556880 | 8/1993 | European Pat. Off. |
| 61-145148 | 2/1986 | Japan |
| 8400956 | 3/1984 | WIPO |
| 8403278 | 8/1984 | WIPO |
| 8404091 | 10/1984 | WIPO |
| 9013535 | 11/1990 | WIPO |
| 9218461 | 10/1992 | WIPO |

OTHER PUBLICATIONS

Investigative Ophthalmology, pp. 455–457, Jun. 1974.
Pharmacological Basis of Therapeutics, Goodman & Gilman, Chapter 9, McMillan Publishing, NY 1980 (6th Ed.).
E.J. of Pharmacol., 100 (1984), 309–319.
Nature, vol. 309, pp. 163–165 (1984).
Current Eye Research, vol. 4, No. 7, pp. 775–780 (1985).
Brit. J. Pharmacol., 100:831–839 (1990).
Science, 245:1118–1121 (1989).
Potter et al, Curr. Eye Res., (1983), 2(10), 711–19.

*Primary Examiner*—Marianne M. Cintins
*Assistant Examiner*—Keith MacMillan
*Attorney, Agent, or Firm*—Hedman, Gibson & Costigan

[57] ABSTRACT

Substituted 5-2-((2-aryl-2-hydroxyethyl)amino)propyl)-1,3-benzodioxoles having the structural formula:

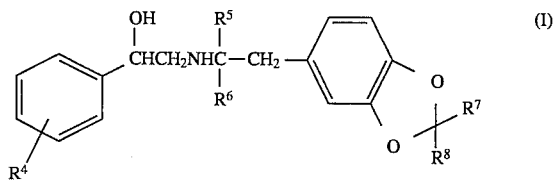

wherein R4, R5, R6, R7, and R8 are as hereinafter defined, are β3-adrenergic agonists useful in the treatment of elevated intraocular pressure and glaucoma.

19 Claims, 5 Drawing Sheets

TREATMENT OF GLAUCOMA AND OCULAR HYPERTENSION WITH β3-ADRENERGIC AGONISTS

BACKGROUND OF THE INVENTION

1. Field of the Invention

The present invention relates to the use of β3-adrenergic agonists for the treatment of glaucoma and ocular hypertension by topical or systemic administration in mammals. More particularly, it relates to the use of ophthalmological compositions containing an active amount of these β3-agonists or the pharmaceutical acceptable salts thereof for the treatment of glaucoma and ocular hypertension.

2. Description of the Prior Art

Glaucoma is an ocular disorder that causes functional or organic disturbances in the eyes due to continuous or repeated increase in intraocular pressure. Not only is there an increase in intraocular pressure, but also optic nerve cupping and visual field loss. Although the pathophysiological mechanism of open angle glaucoma is still unknown there is substantial evidence to suggest that the increased intraocular pressure is detrimental to the eye and that it is the most important factor causing degenerative damage in the retina. Primary open-angle glaucoma is an insidious, slowly progressive, bilateral condition. The condition is often asymmetric on presentation, however, so that one eye may have moderate or advanced damage and the fellow eye has minimal or no detectable damage. Most patients with primary open-angle glaucoma have elevated intraocular pressures in the range of 22 to 40 mm Hg. The cardinal features of open-angle glaucoma include elevated intraocular pressure, cupping and atrophy of the optic disc, and visual field loss. Individuals with intraocular pressures of 21 mm Hg or greater, normal visual fields, normal optic discs, open angles, and the absence of any ocular or systemic disorders contributing to the elevated intraocular pressures are referred to as having ocular hypertension. The concept of ocular hypertension is important because this set of findings occurs in 4% to 10% of the population over age 40. The term normal-tension glaucoma refers to typical glaucomatous optic disc cupping and visual field loss in eyes that have normal intraocular pressures, open angles, and the absence of any contributing ocular or systemic disorders. Normal tension glaucoma may be a consequence of the retina being unusually sensitive to pressure and therefore damage may occur at intraocular pressure levels otherwise considered physiologically normal. The clinical features of normal-tension glaucoma resemble primary open-angle glaucoma except for the absence of elevated intraocular pressure. Some authorities believe the visual field and optic disc changes are identical in normal-tension glaucoma and primary open-angle glaucoma, whereas others state subtle differences exist between the finding of the two conditions. If left untreated, glaucoma almost invariably leads to blindness. The course of the disease is typically slow with progressive loss of vision. Conventional therapy for glaucoma is based on lowering the intraocular pressure, either by drugs, laser therapy, or surgery. The treatment of glaucoma is required to reduce an intraocular pressure to the level adequate to maintain normal optic nerve functions.

Pilocarpine eye drops have been used extensively for the treatment of glaucoma. It is known however that pilocarpine eye drops not only reduce intraocular pressure but also act on the iris sphincter muscle and the ciliary muscle thereby causing side effects such as pupillary constriction, accommodative spasm as well as conjunctival congestion. Such side effects may invite very serious dangers particularly to persons operating motor vehicles. In the case of an elderly patient with cataracts, miosis will result in increased visual impairment.

Epinephrine eye drops are also associated with side effects such as conjunctival congestion, pain at the eyebrow and allergic blepharoconjunctivitis. The eye drops sometimes bring about increased intraocular pressure due to mydriasis.

Recently, beta blockers have become promising in this field, and timolol maleate, levobunolol hydrochloride and betaxolol hydrochloride are commercially available. These drugs are beta-adrenergic antagonists that are believed to work by blocking the β-adrenergic receptors in the ciliary epithelium and, thereby, decrease the production of aqueous humor, the clear fluid that circulates in the eye.

Drug therapy for glaucoma typically comprises topically instilled and/or orally administered medicines. Pilocarpine, epinephrine (and its prodrug form), and β-blockers are frequently used as topical drugs and carbonic anhydrase inhibitors are used via systemic administration. Because of the incidence of significant side-effects associated with conventional medical therapy for glaucoma, there is a serious problem with patient compliance. The discomfort of taking these medicines results in patients not following their treatment schedules.

The problems associated with present commercially available drugs has encouraged development of new agents for the treatment of glaucoma. There is thus a need for the development of new agents which avoids the shortcomings and problems of the presently available medicaments.

SUMMARY OF THE INVENTION

According to the present invention there is provided a method of treating glaucoma and ocular hypertension in a mammal comprising administering to the eye of the mammal or systemically, in an amount effective to reduce intraocular pressure, compounds which act as agonists at $β_3$-adrenergic receptors (also known as $β_3$-adrenoceptors). Such receptors have been described for example by J. R. S. Arch et. al., Nature, 309, 163–165 (1984); C. Wilson et. al., Eur J. Pharmacol., 100, 309–319 (1984); L. J. Emorine et. al, Science 245, 1118–1121 (1989); and A. Bianchetti et. al. Br. J. Pharmacol., 100, 831–839 (1990).

$β_3$-adrenoceptors belong to the family of adrenoceptors which mediate the physiological actions of the hormones adrenaline and noradrenaline. Sub-types of the adrenoceptors, $α_1$-, $α_2$-, $β_1$1-, $β_2$-, and $β_3$- can be identified on the basis of their pharmacological properties and physiological effects. Chemical agents which stimulate or block these receptors (but not $\ominus_3$) are widely used in clinical medicine. More recently, emphasis has been placed upon specific receptor selectivity in order to reduce side effects caused, in part, by interactions with other receptors.

$β_3$-adrenoceptors are known to occur in adipose tissue and the gastrointestinal tract. $β_3$-adrenoceptor agonists have been found to be particularly useful as thermogenic anti-obesity agents and as anti-diabetic agents. Compounds which act as agonists at $β_3$-adrenoceptors may be identified using standard tests. (see for instance C. Wilson et. al., supra).

It has now been found unexpectedly that compounds which act as agonists at $β_3$-adrenoceptors are useful for the treatment of glaucoma and/or ocular hypertension by topical or systemic administration in mammals.

Accordingly the present invention provides a method of treatment of a mammal, including man, suffering from glaucoma or ocular hypertension which comprises administering to the subject an effective amount of a compound which acts as an agonist at $\beta_3$-adrenoceptors.

In a preferred aspect of the present invention, there is provided a method of treatment of a mammal, including man, suffering from a condition of glaucoma and/or ocular hypertension which comprises topically administering to the subject an effective amount of a compound which acts as an agonist at $\beta_3$-adrenoceptors.

In a particularly preferred aspect of the present invention, there is provided a method of treatment of a mammal, including man, suffering from a condition of glaucoma and/or ocular hypertension which comprises systemically administering to the subject orally an effective amount of a compound which acts as an agonist at $\beta_3$-adrenoceptors.

A most particularly preferred aspect of the present invention is directed to the use of $\beta_3$-agonist compounds which have a formula according to compounds I which are described in the present specification.

References in this specification to treatment include prophylactic treatment as well as treatment for the acute and chronic alleviation of symptoms.

Preferred compounds for use according to the invention are those compounds which act as agonists at $\beta_3$-adrenoceptors described in published European Patent Specification Nos. 6735, 21636, 23385, 25331, 28105, 29320, 40000, 40915, 51917, 52963, 61907, 63004, 66351, 68669, 70133, 70134, 82665, 89154, 91749, 94595, 95827, 99707, 101069, 102213, 139921, 140243, 140359, 142102, 146392, 164700, 170121, 170135, 171519, 171702, 182533, 185814, 196849, 198412, 210849, 211721, 233686, 236624, 254532, 254856, 262785, 300290, 303546, 328251, 345591, 386603, 386920, 436435, 455006, 500443, 516349, and 556880;published UK Patent Specification No. 2133986; published PCT Patent Specification Nos. 84/00956, 84/03278, 84/04091, 90/13535 and 92/18461; U.S. Pat. Nos. 4391826, 4585796; published Belgian Patent Specification No. 900983 , published Japanese Patent Specification No. 86-145148, U.S. Pat. Nos. 5,061,727, 5,151,439, 4,707,497, 4,927,836 and application Ser. No. 010,973 filed Jan. 29, 1993.

A preferred group of $\beta_3$-adrenoceptor agonists for use according to the present invention is that represented by the formula (I):

(I)

or a physiologically acceptable salt or ester thereof, wherein $R^4$ represents one or more groups which may be the same or different and are selected from the group consisting of hydrogen, halogen, trifluoromethyl, $C_{1-4}$-alkyl, $C_{1-4}$-alkoxy, $C_{1-4}$-alkylthio, alkoxycarbonyl, carboxyl, hydroxyalkyl, hydroxy, $C_{1-4}$-alkylsulphonyl and $C_{1-4}$-alkylsulphinyl; $R^5$ and $R^6$ each independently represent a hydrogen atom or a $C_{1-4}$-alkyl group; $R^7$ and $R^8$ each independently represent a group selected from the group consisting of hydrogen, carboxy, alkoxycarbonyl, hydroxymethyl, —$CH_2$—$OCH_2$—$CO_2R^9$ and —$CH_2$—$OCH_2$—$CH_2OR^9$, with the proviso that $R^7$ and $R^8$ do not both represent hydrogen; and $R^9$ is a hydrogen atom or a $C_1$–$C_4$ alkyl group.

Particularly preferred $\beta_3$-adrenoceptor agonists and physiologically acceptable salts or solvates thereof for use according to the present invention are listed below. It will be appreciated that where the above compounds of formula (I) and the following specific compounds are optically active, the use of individual enantiomers, diastereoisomers or mixtures thereof, including racemates, is also considered to be within the scope of the present invention.

(R,R)-5-(2-((2-(3-chlorophenyl)-2-hydroxyethyl)amino)-propyl)- 1,3-benzodioxole-2,2-dicarboxylic acid, particularly in the form of its disodium salt;

(R,R)-5-(2-((2-(3-chlorophenyl)-2-hydroxyethyl)amino)-propyl)- 1,3-benzodioxole-2,2-dicarboxylic acid, dimethyl ester;

(R,R)-5-(2-((2-(3-chlorophenyl)-2-hydroxyethyl)amino)-propyl)- 1,3-benzodioxole-2,2-dicarboxylic acid, diethyl ester;

(R,R)-(2-((2-(3-chlorophenyl)-2-hydroxyethyl)amino)-propyl)- 1,3-benzodioxole-2,2-dicarboxylic acid, diisopropyl ester;

(R,S)-5-(2-((2-(3-chlorophenyl)-2hydroxyethyl)amino)-propyl)- 1,3-benzodioxole-2,2-dicarboxylic acid;

(R,R)-(2-((2-(3-chlorophenyl)-2hydroxyethyl)amino)-propyl)- 1,3-benzodioxole-2,2-dicarboxylic acid, bis((1-methylethyl)ester hydrochloride.

In a further aspect, the present invention provides a therapeutic agent which comprises an effective amount of a compound which acts as an agonist at $\beta_3$-adrenoceptors for use in medicine. The $\beta_3$ agonists of Formula (I) have little or no $\beta_1$ or $\beta_2$ agonist activity and thus are substantially free of $\beta_1$ or $\beta_2$ agonist activity. For example (R,R) -5-(2-((2-(3-chlorophenyl)- 2-hydroxyethyl)amino)propyl)-1,3-benzodioxole- 2,2-dicarboxylic acid, particularly in the form of its disodium salt has been shown to have no binding to human $\beta_1$ or $\beta_2$ receptors expressed in chinese hamster ovary cells.

Also according to the present invention there is provided a method of treating glaucoma and ocular hypertension in humans or other mammals which comprises administering to a human or other mammal an antiglaucoma or ocular antihypertensive effective amount of a $\beta_3$ compound of the present invention.

Further, according to the present invention there are provided pharmaceutical compositions of matter comprising an effective amount of a $\beta_3$ compound of the present invention in combination with a pharmaceutically acceptable carrier.

DETAILED DESCRIPTION OF THE INVENTION

This invention provides a method of treating glaucoma or ocular hypertension. The method comprises either topical ocular or oral dosing with a composition comprising an effective intraocular pressure reducing amount of $\beta_3$-adrenergic agonist chosen from 5-(2-((2-aryl- 2-hydroxyethyl)amino)propyl)-1,3-benzodioxoles.

In a series of experiments in a glaucomatous monkey model, compositions according to the invention are administered either intravenously or topically to an animal eye and the intraocular pressure in the experimental eye is compared to controls. The results of the comparative tests are presented in FIG. 1 to FIG. 5. The compound (R,R)-(5-(2-((2-(3-chlorophenyl)-2-hydroxyethyl)amino)propyl)- 1,3-benzodioxole-2,2dicarboxylic acid disodium salt is found to lower intraocular pressure in glaucomatous monkeys following both intravenous and topical ocular administration.

The effect of (R,R)-(5-(2-((2-(3-chlorophenyl)- 2-hydroxyethyl)amino)propyl)-1,3-benzodioxole- 2,2-dicarboxylic acid disodium salt on intraocular pressure is shown in Table I in which seven cynomolgus monkeys with laser induced glaucoma are treated. The procedures for the laser induced glaucoma are published in the following articles: Gaasterland D. and Kupfer C, Invest. Ophthalmol 13: 455–457(1974) and Lee P. Y., Podos S. M., Howard-Williams J. R., Severin C. H., Rose A. D., Siegel M. J., Curr Eye Res 4: 775–781(1985). The intraocular pressure is measured over 2 days during the same 6 hour interval. On day 1, a baseline diurnal intraocular pressure time course is measured. On day 2, three baseline intraocular pressure measurements are made over 2 hours, after which the drug is injected intravenously as a 0.1% aqueous solution of 1 mg/kg in normal saline. The intraocular pressure is subsequently measured at 0.5, 1, 2, 3 and 4 hours post-injection. The mean value of the first 3 intraocular pressure measurements on each day is used as the control intraocular pressure. There is no statistically significant difference ($p>0.1$) between the control intraocular pressure measured on Day 1 (35.2±1.8 mm Hg) and the baseline intraocular pressure measured on Day 2 (36.5±2.5 mm Hg).

TABLE I

|  | IOP | CHANGE IN IOP FROM BASELINE | p value* | Percent Change |
|---|---|---|---|---|
| Day 1 | | | | |
| baseline control | 35.2 | | | |
| 30 minutes | 37.1 | 2.0 | 0.031 | +6 |
| 1 hour | 38.3 | 3.1 | 0.023 | +9 |
| 2 hours | 37.4 | 2.2 | 0.022 | +6 |
| 3 hours | 38.4 | 3.2 | 0.043 | +9 |
| 4 hours | 36.1 | 1.0 | 0.644 | +3 |
| Day 2 | | | | |
| baseline control | 36.5 | | | |
| 30 minutes | 33.9 | −2.7 | 0.124 | −8 |
| 1 hour | 33.6 | −3.0 | 0.024 | −9 |
| 2 hours | 34.3 | −2.3 | 0.079 | −7 |
| 3 hours | 35.9 | −0.7 | 0.602 | −2 |
| 4 hours | 34.1 | −2.4 | 0.155 | −6 |

*paired t-test, 2-sided

Figure 1:
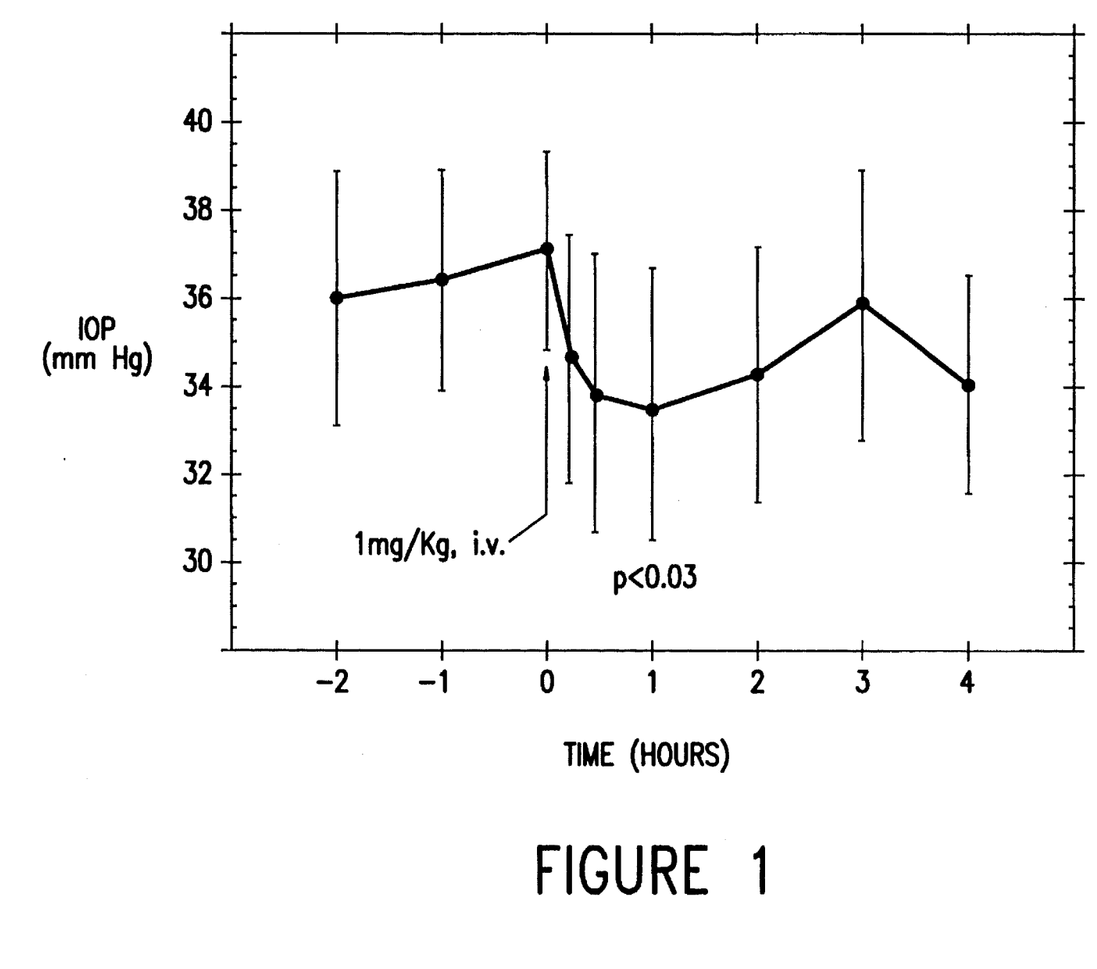
FIG. 1: Pre and post-drug intraocular pressure (mean±sem n=7) measured in glaucomatous eyes of glaucomatous monkeys indicating a decrease in intraocular pressure following intravenous injection of (R,R)-5-(2-((2-(3-chlorophenyl)-2-hydroxyethyl)amino)propyl)- 1,3-benzodioxole-2,2-dicarboxylic acid, disodium salt.
Figure 2:
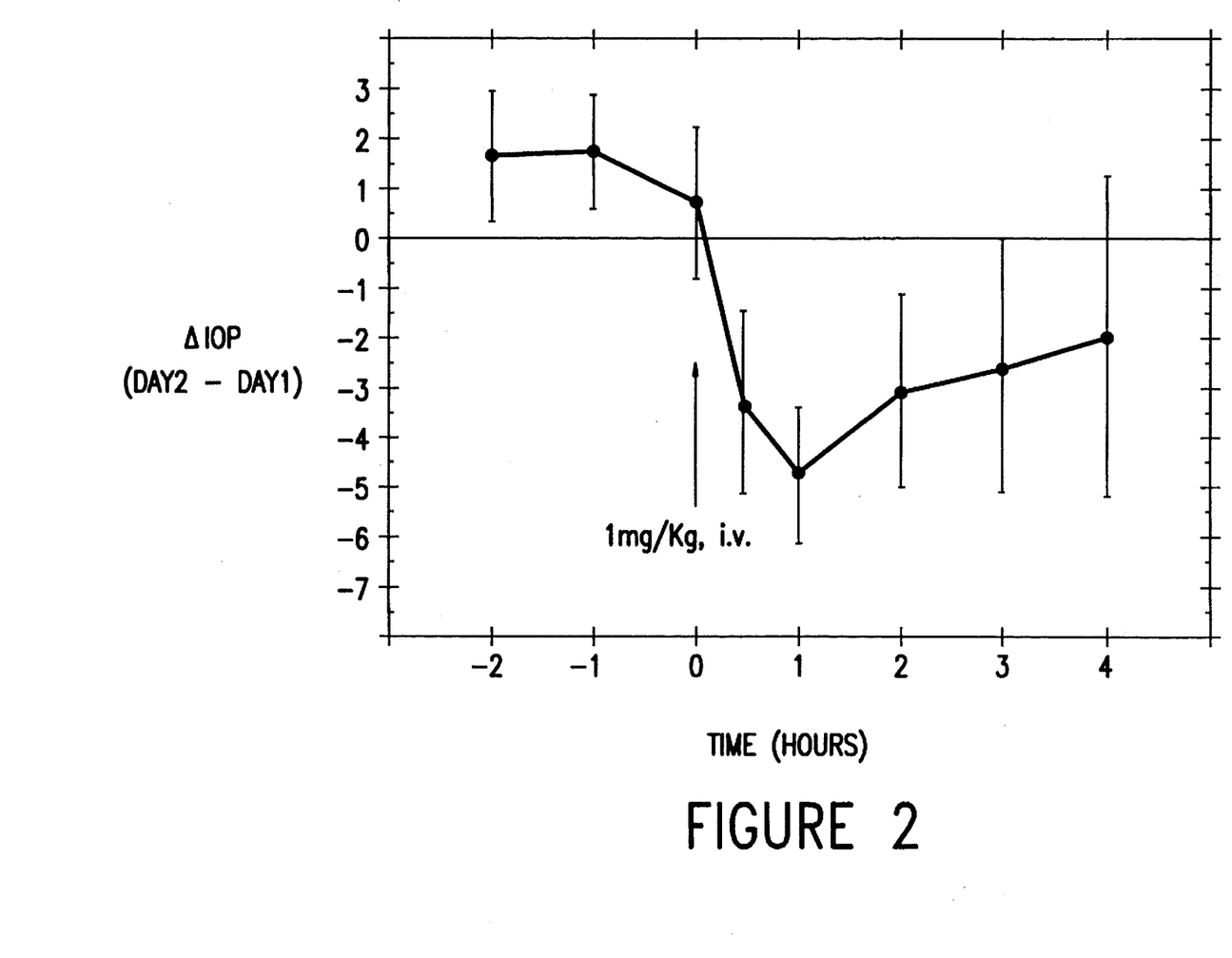
FIG. 2: The difference in intraocular pressure (mean±sem n=7)comparing intraocular pressure on day 2 following intravenous injection of (R,R)-5-(2-((2-(3-chlorophenyl)-2-hydroxyethyl)amino)propyl)-1,3-benzodioxole- 2,2-dicarboxylic acid, disodium salt to that on day 1 with no drug administration.
Figure 3:
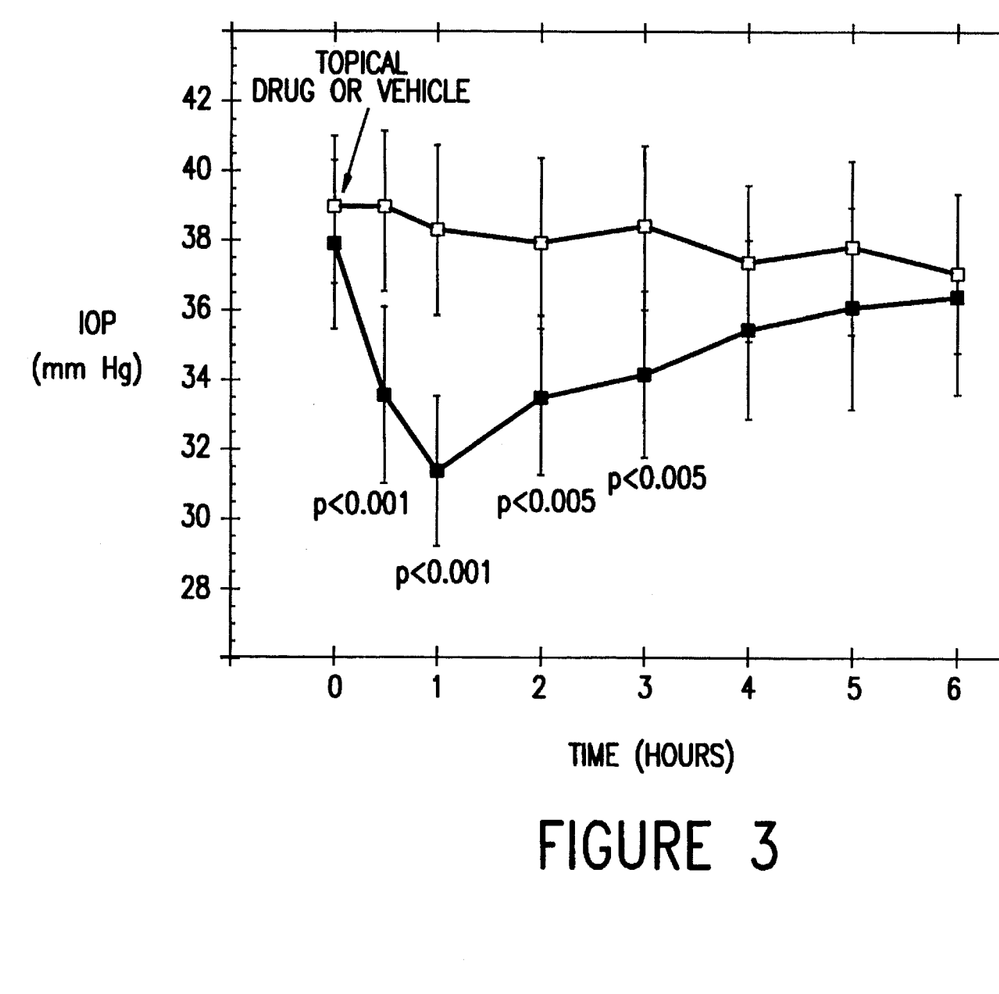
FIG. 3: The intraocular pressure lowering effect of topical ocular administration of 50 µl of 0.5% (R,R)-5-(2-((2-(3-chlorophenyl)-2-hydroxyethyl)amino)propyl)- 1,3-benzodioxole-2,2-dicarboxylic acid disodium salt to 8 glaucomatons cynomolgus monkey eyes (mean±sem).
Figure 4:
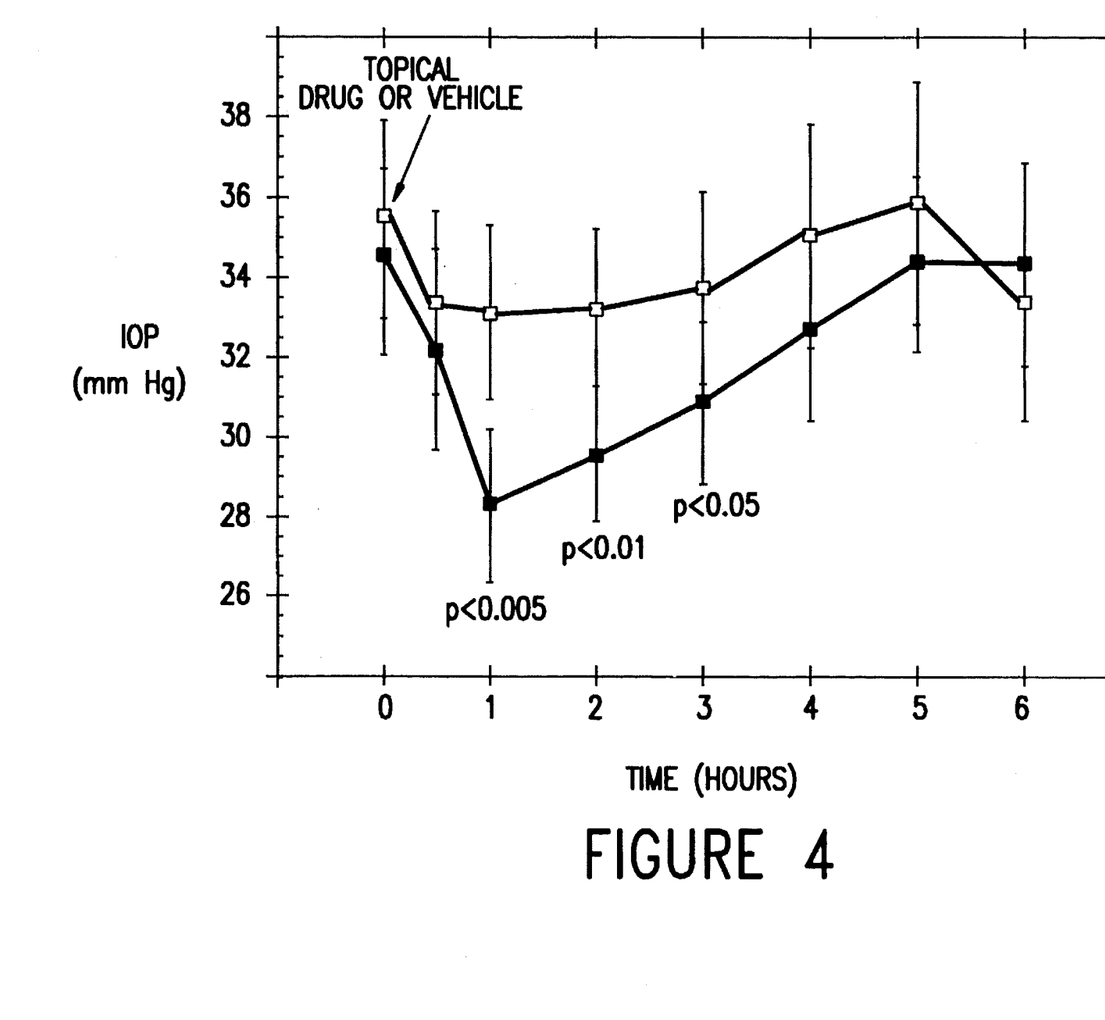
FIG. 4: The intraocular pressure lowering effect of topical administration of 50 µl of 1% (R,R)-5-( 2-((2-(3-chlorophenyl)-2-hydroxyethyl)amino)propyl)- 1,3-benzodioxole-2,2-dicarboxylic acid disodium salt to 8 glaucomatous cynomolgus monkey eyes (mean±sem).
Figure 5:
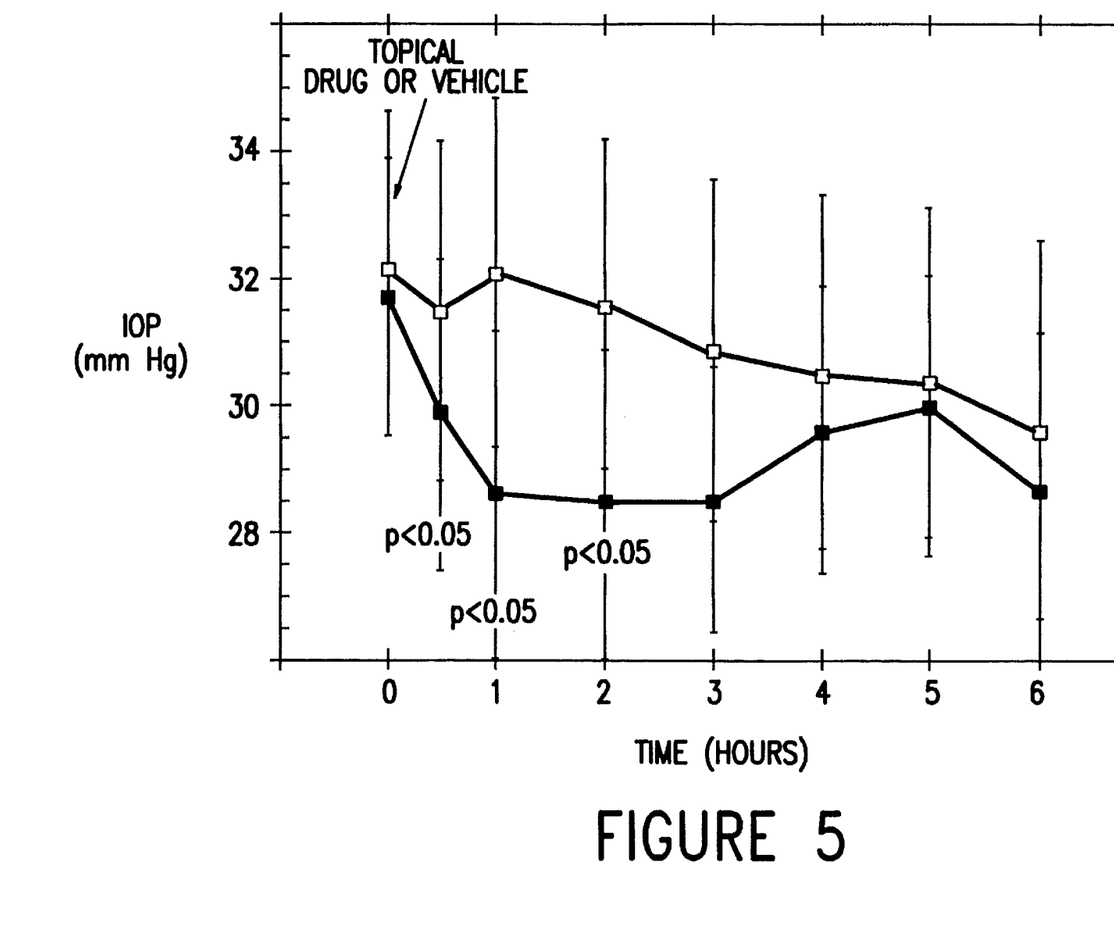
FIG. 5: The intraocular pressure lowering effect of topical administration of 50 µl of 1% (R,R)-( 5-(2-((2-(3-chlorophenyl)-2-hydroxyethyl)amino)propyl)- 1,3-benzodioxole-2,2-dicarboxylic acid bis(1-methylethyl)ester hydrochloride to 8 glaucomatous cynomolgus monkey eyes (mean±sem).

The intraocular pressure on day 1 tends to increase slightly over the course of the day (TABLE 1). Whereas on day 2, intraocular pressure decreased after the injection of (R,R)-(5-(2-((2-(3-chlorophenyl)-2-hydroxyethyl)amino)-propyl)- 1,3-benzodioxole-2,2-dicarboxylic acid disodium salt, (FIG. 2). The statistically significant difference in intraocular pressure on day 2 following drug administration compared to day 1 in which no drug is administered (intraocular pressure day 2 minus intraocular pressure day 1) indicates a decrease in intraocular pressure following intravenous injection of the test compound (FIG. 2, TABLE 1). Following topical ocular administration of 0.5% and 1% (R,R)-(5-(2-((2-(3-chlorophenyl)-2-hydroxyethyl)amino)-propyl)- 1,3-benzodioxole-2,2-dicarboxylic acid disodium salt to glaucomatous monkeys, the intraocular pressure is found to decrease (FIG. 3 and FIG. 4). Topical ocular administration of 1% (R,R)-(5-( 2-((2-(3-chlorophenyl)-2-hydroxyethyl)amino)propyl)- 1,3-benzodioxole-2,2-dicarboxylic acid bis(1-methylethyl) ester hydrochloride to glaucomatous monkeys is found to cause a statistically significant reduction in intraocular pressure compared to the vehicle control intraocular pressure at 30 minutes, 1 hour and 2 hours after administration (FIG. 5).

The pharmaceutical compositions of the invention are administered in the form of ophthalmic pharmaceutical compositions adapted for topical administration to the eye, such as solutions, suspensions, ointments and solid inserts or standard pharmaceutical compositions for systemic administration, in the form of tablets, capsules or intravenous injections for both instantaneous and controlled release. Topical ophthalmic formulations of the invention may contain $\beta_3$ agonists in an amount from about 0.001 to about 15% (w/v %) and especially about 0.05 to about 5% of medicament. As a unit dosage form, an amount of $\beta_3$ agonist from between about 500 ng to 7.5 mg, preferably 0.05 mg to 2.5 mg of the active substance applied topically to the human eye. These doses can be administered as a single daily dose or on a 2 to 4 dose per day regimen. Systemically administered formulations may contain $\beta_3$ agonists in an amount from about 1 mg to about 2000 mg and especially about 5 mg to 1500 mg. as a single daily dose or on a 2 to 4 dose per day regimen.

Where utilized herein, the term "controlling the elevated intraocular pressure" means the regulation, attenuation and modulation of increased intraocular tension e.g., the primary diagnostic symptom of the disease glaucoma. The term also means that the diminution, in the otherwise elevated intraocular pressure, obtained by the practice of the invention is maintained for a significant period of time as, for example, between consecutive doses of the composition of the invention.

The $\beta_3$ agonists may be employed in the composition and methods of the invention as the sole IOP lowering ingredient or may be used in combination with other mechanistically distinct IOP lowering ingredients such as beta adrenergic blocking agents, (e.g., timolol), carbonic anhydrase inhibitors, miotic agents (e.g., pilocarpine), epinephrine and dipivalylepinephrine, $\alpha_2$ adrenergic agonists prostaglandins or prostaglandin analogs. For the purposes of the present invention, the term beta-adrenergic blocker means a compound which by binding to $\beta$-1 or $\beta$-2 adrenergic receptors reduces or eliminates sympathetic activity or blocks the effects of exogenously administered catecholamines or adrenergic drugs mediated via these receptors. See, for example, Weiner, N., Drugs That Inhibit Adrenergic Nerves and Block Adrenergic Receptors, in The Pharmaceutical Basis of Therapeutics (ed. A. G. Goodman, L. S. Goodman, A. Gilman), Macmillan Publishing, New York, 1980, 6th ed., pp. 188–197.

The present invention therefore also provides a pharmaceutical formulation suitable for use in reducing intraocular pressure or for treating glaucoma which formulation comprises a novel compound of formula (I) and a pharmaceutically acceptable carrier.

It will be understood that any formulation may further comprise another active ingredient such as another antiglaucoma agent for example a topical carbonic anhydrase inhibitor or a topical $\beta$-adrenergic blocking agent.

The active drugs of this invention are most suitably administered in the form of tablets or capsules for oral administration or in the form of ophthalmic pharmaceutical compositions adapted for topical administration to the eye such as a solution, suspension, ointment, or as a solid insert. For oral administration, the drug can be employed in any of the usual dosage forms either in a comtemporaneous delivery system or sustained release form. Any number of the usual excipients or tableting aids can likewise be included. A preferred composition for topical ophthalmic administration is eye drops. Formulations of these compounds may contain from 0.001 to 15% and especially 0.05% to 5% of medicament, which corresponds to dosages from between 500 ng to 7.5 mg, preferably 0.05 to 2.5 mg, generically applied to the human eye, generally on a daily basis in single or divided doses so long as the condition being treated exists. Higher dosages as, for example, about 10% or lower dosages can be employed provided the dose is effective in reducing or controlling elevated intraocular pressure.

This invention therefore further provides a sterile pharmaceutical formulation adapted for topical administration to the eye which formulation comprises a compounds of formula (I) and a carrier suitable for topical administration. These herein before described dosage values are believed accurate for human patients and are based on the known and presently understood pharmacology of the compounds, and the action of other similar entities in the human eye. As with all medications, dosage requirements are variable and must be individualized on the basis of the disease and the response of the patient.

For topical administration, pharmaceutically acceptable carriers are, for example, water, mixtures of water and water-miscible solvents such as lower alkanols or arylalkanols, conventional phosphate buffer vehicle systems, isotonic boric acid vehicles, isotonic sodium chloride vehicles, isotonic sodium citrate vehicles, isotonic sodium acetate vehicles, vegetable oils, polyalkylene glycols, petroleum based jelly, as well as aqueous solutions containing ethyl cellulose, carboxymethylcellulose, hydroxypropylmethylcellulose, hydroxyethylcellulose, carbopol, polyvinyl alcohol, polyvinylpyrrolidone, isopropyl myristate and other conventionally-employed non-toxic, pharmaceutically acceptable orqanic and inorganic carriers. The pharmaceutical preparation may also contain non-toxic auxiliary substances such as emulsifying agents, wetting agents, bodying agents and the like, as for example, polyethylene glycols 30, 200, 300, 400 and 600, carbowaxes 1,000,1,500, 4,000, 6,000 and 10,000, and polysorbate 80. Antibacterial and preservative components can also be employed in the topical ophthalmic formulation, as for example, benzalkonium chloride, and other quaternary ammonium preservative agents, phenylmercuric salts, sorbic acid, chlorobutanol, disodium edetate, thimerosal, methyl and propyl paraben, benzyl alcohol, and phenyl ethanol. Osmotic agents and buffering ingredients which may be employed in the topical ophthalmic formulation include sodium chloride, mannitol, sodium borate, sodium acetates, sodium phosphates, gluconate buffers, sodium hydroxide and hydrochloric acid. Other conventional ingredients can be employed such as sorbitan monolaurate, triethanolamine, oleate, polyoxyethylene sorbitan 35 monopalmitylate, dioctyl sodium sulfosuccinate, monothioglycerol, thiosorbitol, ethylenediamine tetraacetic acid, and the like.

Pharmaceutically suitable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

The pharmaceutical formulation may also be in the form of a solid insert such as one which after dispensing the drug remains essentially intact, or a bio-erodible insert that is soluble in lacrimal fluids or otherwise disintegrates.

What is claimed is:

1. A method of treating glaucoma or ocular hypertension in a mammal in need of such treatment which comprises topically administering to the eye of a mammal or systemically administering to a mammal a $\beta_3$-adrenoceptor agonist in an amount effective to reduce intraocular pressure.

2. A method of treating glaucoma or intraocular hypertension in a patient in need of such treatment which comprises topically administering to the eye of a mammal or systemically administering to a mammal in an amount effective to reduce intraocular pressure, a compound having the formula:

or a physiologically acceptable salt or ester thereof, wherein $R^4$ represents one or more groups which may be the same or different and are selected from the group consisting of hydrogen, halogen, trifluoromethyl, $C_{1-4}$-alkyl, $C_{1-4}$-alkoxy, $C_{1-4}$-alkylthio, alkoxycarbonyl, carboxyl, hydroxyalkyl, hydroxy, $C_{1-4}$, alkylsulphonyl and $C_{1-4}$,-alkylsulphinyl; $R^5$ and $R^6$ each independently represent a hydrogen atom or a $C_{1-4}$-alkyl group; $R^7$ and $R^8$ each independently represent a group selected from the group consisting of hydrogen, carboxy, alkoxycarbonyl, hydroxymethyl, —CH$_2$-OCH$_2$-CO$_2$R$^9$ and —CH$_2$—OCH$_2$—CH$_2$OR$^9$, with the proviso that R$^7$ and R$^8$ do not both represent hydrogen; and R$^9$ is a hydrogen atom or a C$_1$–C$_4$ alkyl group.

3. The method of claim 2 wherein the compound is (R,R)-5-(2-((2-(3-chlorophenyl)-2-hydroxyethyl)amino)-propyl)- 1,3-benzodioxole-2,2-dicarboxylic acid, dimethyl ester.

4. The method of claim 2 wherein the compound is (R,R)-5-(2-((2-(3-chlorophenyl)-2-hydroxyethyl)amino)-propyl)- 1,3-benzodioxole-2,2-dicarboxylic acid, diethyl ester.

5. The method of claim 2 wherein the compound is (R,R)-5-(2-((2-(3-chlorophenyl)-2-hydroxyethyl)amino)-propyl)- 1,3-benzodioxole-2,2-dicarboxylic acid, diisopropyl ester.

6. The method of claim 2 wherein the compound ms (R,R)-5-(2-((2-(3-chlorophenyl)-2-hydroxyethyl)amino)-propyl)- 1,3-benzodioxole-2,2-dicarboxylic acid, disodium salt.

7. The method of claim 2 wherein the compound is (R,R)-5-(2-((2-(3-chlorophenyl)-2-hydroxyethyl)amino)-propyl)- 1,3-benzodioxole-2,2-dicarboxylic acid.

8. The method of claim 2 wherein the compound is (R,R)-(2-((2-(3-chlorophenyl)-2-hydroxyethyl)amino)propyl)- 1,3-benzodioxole-2,2-dicarboxylic acid, bis(1-methylethyl) ester hydrochloride.

9. A sterile opthalmologically acceptable composition for the treatment of glaucoma and ocular hypertension comprising an effective amount of a compound selected from the group consisting of those of the formula:

or a physiologically acceptable salt or ester thereof, wherein R$^4$ represents one or more groups which may be the same or different and are selected from the group consisting of hydrogen, halogen, trifluoromethyl, C$_{1-4}$-alkyl, C$_{1-4}$-alkoxy, C$_{1-4}$-alkylthio, alkoxycarbonyl, carboxyl, hydroxylalkyl, hydroxy, C$_{1-4}$-alkylsulphonyl, and C$_{1-4}$ alkylsulphinyl; R$^5$ and R$^6$ each independently represent a hydrogen atom or a C$_{1-4}$-alkyl group; R$^7$ and R$^8$ each independently represent a group selected from the group consisting of hydrogen, carboxy, alkoxycarbonyl, hydroxymethyl, —CH$_2$—OCH$_2$—CO$_2$R$^9$ and —CH$_2$—OCH$_2$—CH$_2$OR$^9$, with the proviso that R$^7$ and R$^8$ do not both represent hydrogen; and R$^9$ is a hydrogen atom or a C$_{1-4}$ alkyl group at a concentration of 0.001% to 15% in an isotonic pharmaceutical vehicle comprising water, and a buffer.

10. The composition of claim 9 wherein the compound is (R,R)-5-(2-((2-(3-chlorophenyl)-2-hydroxyethyl)amino)-propyl)- 1,3-benzodioxole-2,2-dicarboxylic acid, dimethyl ester.

11. The composition of claim 9 wherein the compound is (R,R)-5-(2-((2-(3-chlorophenyl)-2-hydroxyethyl)amino)-propyl)- 1,3-benzodioxole-2,2-dicarboxylic acid, diethyl ester.

12. The composition of claim 9 wherein the compound is (R,R)-5-(2-((2-(3-chlorophenyl)-2-hydroxyethyl)amino)-propyl)- 1,3-benzodioxole-2,2-dicarboxylic acid, diisopropyl ester.

13. The composition of claim 9 wherein the compound is (R,R)-5-(2-((2-(3-chlorophenyl)-2-hydroxyethyl)amino)-propyl)- 1,3-benzodioxole-2,2-dicarboxylic acid, disodium salt.

14. The composition of claim 9 wherein the compound is (R,R)-5-(2-((2-(3-chlorophenyl)-2-hydroxyethyl)amino)-propyl)- 1,3-benzodioxole-2,2-dicarboxylic acid.

15. The composition of claim 9 wherein the compound is (R,R)-(2-((2-(3-chlorophenyl)-2-hydroxyethyl)amino)propyl)- 1,3-benzodioxole-2,2-dicarboxylic acid, bis(1-methylethyl) ester hydrochloride.

16. A method of treating glaucoma as defined in claim 1 which comprises topically administering to the eye of a mammal a β$_3$-adrenoreceptor agonist in an amount effective to reduce intraocular pressure.

17. A method of treating glaucoma as defined in claim 1 which comprises systemically administering to the eye of a mammal a β$_3$-adrenoreceptor agonist in an amount effective to reduce intraocular pressure.

18. A method of treating ocular hypertension as defined in claim 1 which comprises topically administering to the eye of a mammal a β$_3$-adrenoreceptor agonist in an amount effective to reduce intraocular pressure.

19. A method of treating ocular hypertension as defined in claim 1 which comprises topically administering to the eye of a mammal a β$_3$-adrenoreceptor agonist in an amount effective to reduce intraocular pressure.

* * * * *